United States Patent [19]

Date et al.

[11] Patent Number: 5,319,958

[45] Date of Patent: Jun. 14, 1994

[54] APPARATUS AND METHOD FOR EVALUATING PHASE CHANGE OF EMULSION

[75] Inventors: Munehiro Date, Wako; Yukio Inada, Tokyo, both of Japan

[73] Assignee: Rikagaku Kenkyusho, Wako, Japan

[21] Appl. No.: 51,814

[22] Filed: Apr. 26, 1993

Related U.S. Application Data

[63] Continuation-in-part of Ser. No. 668,907, Mar. 13, 1991, abandoned.

[30] Foreign Application Priority Data

| Mar. 13, 1990 | [JP] | Japan | 2-61883 |
| Jun. 8, 1990 | [JP] | Japan | 2-151132 |
| Jun. 28, 1990 | [JP] | Japan | 2-170790 |
| Jan. 22, 1991 | [JP] | Japan | 3-005949 |

[51] Int. Cl.$^5$ .................................. G01N 11/02
[52] U.S. Cl. .......................... 73/53.01; 73/54.39
[58] Field of Search ....................... 73/53.01, 54.39

[56] References Cited

U.S. PATENT DOCUMENTS

| 2,865,197 | 12/1958 | Pentler et al. | 73/58 |
| 3,282,091 | 11/1966 | Webb | 73/59 |
| 3,901,069 | 8/1975 | Van Gastel | 73/58 |
| 4,095,461 | 6/1978 | Starita | 73/794 |
| 4,109,514 | 8/1978 | Thomas | 73/54.22 |
| 4,166,381 | 9/1979 | Woo | 73/54 |
| 4,167,110 | 9/1979 | Kopito | 73/54.22 |
| 4,512,182 | 4/1985 | Rizvi et al. | 73/64.1 |
| 4,555,278 | 11/1985 | Cescon et al. | 149/21 |
| 4,799,453 | 1/1989 | Nobbs et al. | 118/33 |
| 4,854,175 | 8/1989 | Budhu | 73/841 |
| 4,862,735 | 9/1989 | Williams et al. | 73/54 |
| 4,911,770 | 3/1990 | Oliver | 149/21 |
| 4,930,346 | 6/1990 | Paakkinen | 73/59 |

FOREIGN PATENT DOCUMENTS

| 2706855 | 8/1977 | Fed. Rep. of Germany . |
| 3262941 | 11/1991 | Japan . |
| 443941 | 2/1992 | Japan . |
| 460438 | 2/1992 | Japan . |
| 1534371 | 1/1990 | U.S.S.R. | 73/841 |
| 1376104 | 12/1974 | United Kingdom | 73/60 |
| 2013903 | 8/1979 | United Kingdom . |

OTHER PUBLICATIONS

R. L. Imken, "analysis of cure behaviour", IBM Technical Disclosure Bulletin, vol. 26, No. 12, May 1984, pp. 6471–6472.

*Primary Examiner*—Michael J. Tokar
*Assistant Examiner*—Raymond Y. Mah
*Attorney, Agent, or Firm*—Cushman, Darby & Cushman

[57] ABSTRACT

An apparatus for evaluating phase change of an emulsion comprises a sliding part having a sliding surface to which the emulsion is applied, a pushing part disposed at a fixed position and pushed against the sliding surface applied with the emulsion, and sensor means for measuring a force imparted to the pushing part in the sliding direction. Also disclosed is a method for evaluating phase change of an emulsion from changes in the force measured by the apparatus.

18 Claims, 11 Drawing Sheets

W/O TYPE

APPARATUS AND METHOD FOR EVALUATING PHASE CHANGE OF EMULSION

This is a continuation-in-part of application Ser. No. 07/668,907, filed on Mar. 13, 1991, now abandoned.

FIELD OF THE INVENTION

The present invention relates to an apparatus and a method for evaluating phase change of an emulsion.

BACKGROUND OF THE INVENTION

Emulsions are mixtures of two or more incompletely miscible liquids such as oil and water. There are many kinds of emulsions in use in the modern world. Some, such as milk, mayonnaise, creams for foods, cosmetic creams and the like, are used in the home. Others, such as paints, adhesives, drugs, pesticides, asphalt and the like, are utilized in industry.

If an emulsion is left to stand without agitation for a long period, it will generally separate into its two or more constituent liquids by creaming, cohesion and coalescence of its dispersed droplets. It is therefore important for industrial use of emulsions to be able to evaluate their chemical stability as well as their mechanical properties such as hardness, fluidity and deformability.

Some emulsions such as cosmetic creams, nutrient creams and butters are not stable during the use, and the evaluation of such emulsions has conventionally depended on tactile tests conducted by skilled panalers. Although human sensitivity is very high and such evaluations are generally accurate, they involve some disadvantages. Specifically, they are strongly influenced by the panelers' physical condition, individual preferences, the test environment, and so on. Therefore the data sometimes vary widely and are not always reliable.

SUMMARY OF THE INVENTION

It is therefore an object of the invention to provide an apparatus and a method for evaluating phase change of emulsions, which can continuously analyze changes in the mechanical properties of the emulsion during phase change and can provide objective evaluations not dependent on the physical sensations of humans.

The present invention provides an apparatus for evaluation phase change of an emulsion comprising a sliding part having a sliding surface to which the emulsion is applied, a pushing part disposed at a fixed position and pushed against the sliding surface applied with the emulsion, and sensor means for measuring the force imparted to the pushing part in the sliding direction, phase change of the emulsion being evaluated from changes in the measured force.

The present invention also provides a method for evaluating phase change of an emulsion comprising applying the emulsion to the sliding surface of a sliding part, sliding the sliding part in parallel with the sliding surface, pushing a pushing part disposed at a fixed position against the sliding surface applied with the emulsion present between the pushing part and the sliding surface, measuring the force imparted to the pushing part in the sliding direction, and evaluating phase change of the emulsion from changes in the measured force.

The above and other objects and features of the present invention will become apparent from the following description of preferred embodiments taking reference to the accompanying drawings.

DESCRIPTION OF THE PREFERRED EMBODIMENTS

Figure 1:
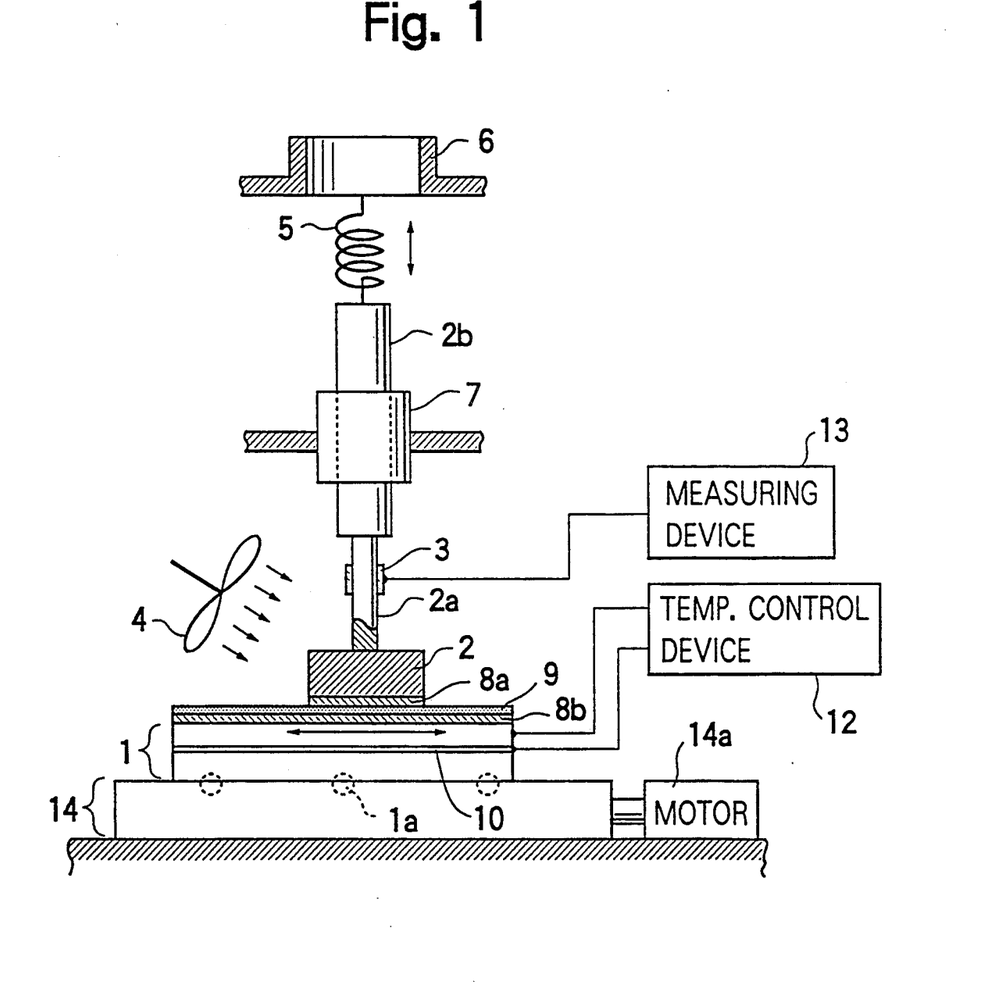
FIG. 1 is a schematic view of an apparatus in accordance with one embodiment of the present invention.

FIG. 1 shows an apparatus in accordance with a first embodiment of the present invention.

In FIG. 1, the horizontally movable part 1 is mounted by means of sliding bearings 1a. Film-like heater 10 is embedded in movable plate 1. A temperature control device 12 is connected to heater 10. Control device 12 includes a conventional thermocouple for detecting the temperature of movable plate 1, and a controller for controlling the temperature of the movable plate 1 heated by the heater 10 to between −20° C. and 100° C. Drive mechanism 14 including a motor 14a is provided to reciprocate the movable plate 1 along the surface of the pushing part 2. A measuring device 13, which indicates the strain detected by gauge 3, is provided for measuring the force imparted to the pushing part in a sliding direction.

Reference numerals 8a and 8b designate polymer films, which are attached to surfaces of the pushing part 2 and the movable plate 1, respectively. The lower surface of the film 8a on pushing part 2 is pressed through emulsion 9 against film 8b on movable plate 1 at a substantially constant pressure by spring 5. The phase change or inversion of emulsion 9 is gradually effected, depending on the operating condition of the apparatus, such as the speed of the sliding movement, the temperature, the air blowing thereon, etc. Emulsion 9 is interposed between film 8a and film 8b and is subjected to shearing action under the substantially constant pressure through the pushing part 2 by the spring 5. During movement of part 1, the thickness of emulsion 9 varies, i.e. decreases. The gap or space between films 8a, 8b, however, can vary (decrease) in accordance with the reduction of the thickness of emulsion 9, owing to the vertical displacement of pushing part 2. Thus, the surface of film 8a is kept in constant contact with emulsion 9 so as to induce phase change of emulsion 9, while a substantially constant pressure acts on emulsion 9. The force that acts on the pushing part 2 in a sliding direction, can be measured through the strain gauge 3 by the measuring device 13.

Films 8a and 8b are not necessarily disposed on the surfaces of plate 1 and part 2. Either film may be disposed on either of the surfaces, or neither may be disposed on the surfaces.

The pushing part 2 is rigidly connected to a vertical shaft 2a which is in turn connected to an enlarged shaft 2b extending vertically upward. The film of polymer substance 8a is preferably attached to the bottom surface of the pushing part 2. The shaft 2b is vertically slidably supported by a bearing portion 7 fixed to a stationary part (not shown). The bottom end of a vertically oriented coil spring 5 is attached to the top end of the shaft 2b and the top end of the spring 5 is attached to the bottom end of an up-and-down mechanism 6. The body of the up-and-down mechanism 6 is disposed on a stationary part (not shown) and the mechanism is adapted to move the shafts 2a and 2b up and down through the spring 5. The force of the spring 5 pushes the pushing part 2 or the attached film against the sliding surface of the movable plate 1 or the attached film to which the emulsion has been applied.

The sensor means or strain gauge 3 is attached to the surface of the shaft 2a and adapted to measure the force imparted to the pushing part 2 in the sliding direction. The sensor means need not necessarily be a strain gauge and any of various other well-known measuring devices can alternatively be used for measuring the force. A fan 4 is preferably positioned laterally of the pushing part 2 for blowing air onto the emulsion to volatilize its volatile components.

The procedure for using the apparatus is as follows.
(1) the emulsion is applied to the sliding surface of the movable plate 1 or to the attached film thereof,
(2) the movable plate 1 is reciprocated in parallel with the sliding surface by the drive mechanism (not shown),
(3) the pushing part 2 and the attached film thereof are pushed against the sliding surface by the up-and-down mechanism 6 with the emulsion present between the pushing part 2 and the sliding surface or between the attached films thereof,
(4) the force imparted to the pushing part 2 in the sliding direction is measured by the sensor 3, and
(5) phase change of the emulsion is evaluated from changes in the measured value.

The evaluation can be made by comparing the measured force with standard data, as shown later in the examples.

Figure 2:
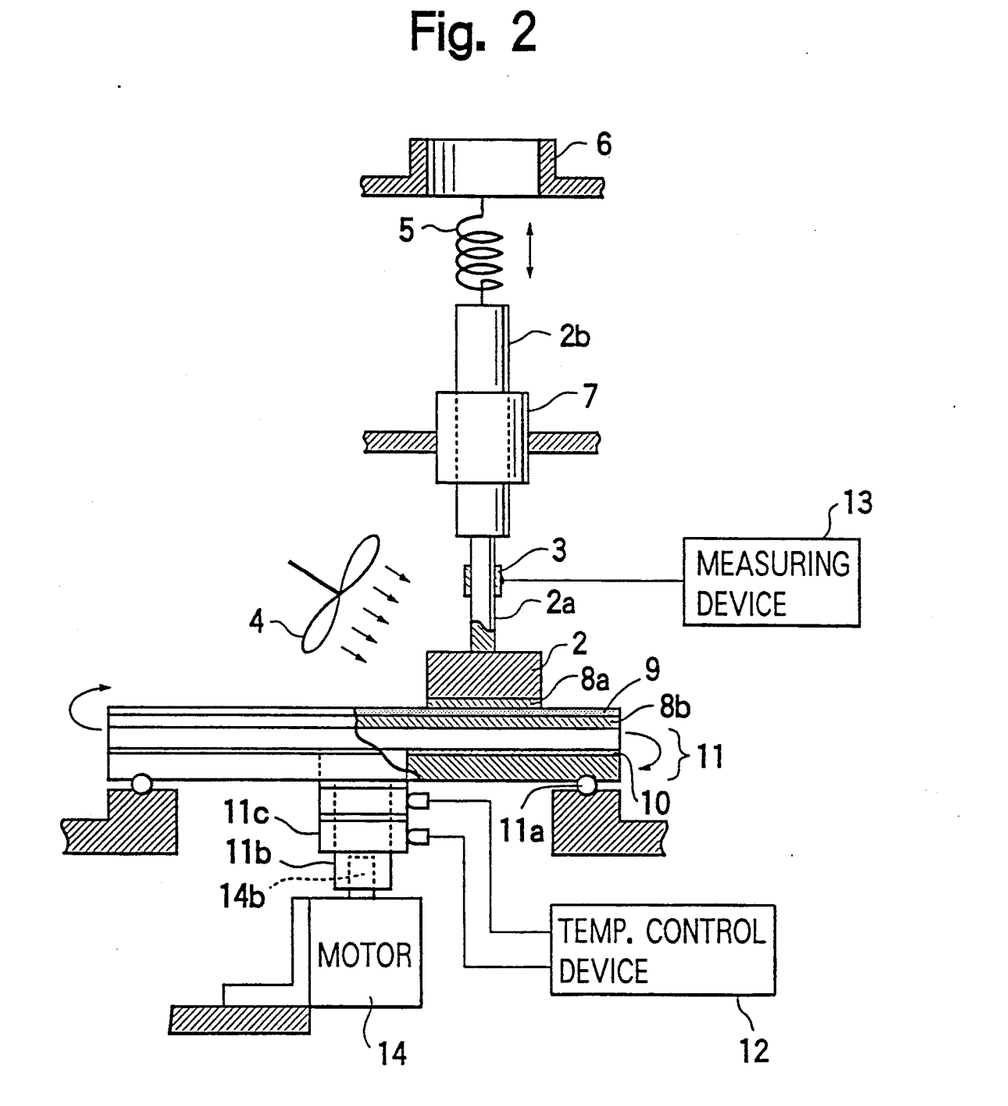
FIG. 2 is a schematic view of an apparatus in accordance with another embodiment of the present invention.
Figure 3:
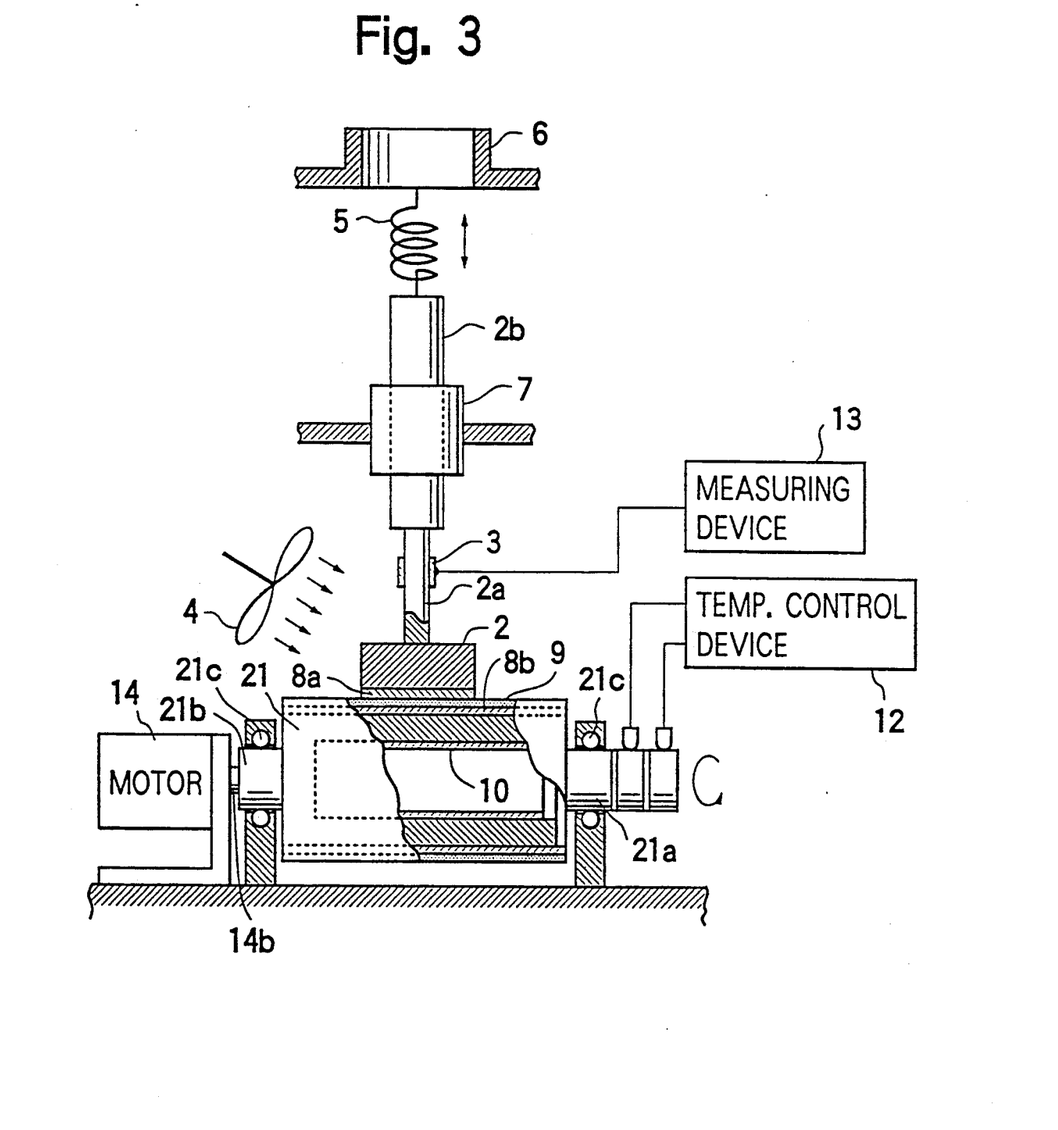
FIG. 3 is a schematic view of an apparatus in accordance with another embodiment of the present invention.

FIGS. 2 and 3 show two other apparatuses in accordance with the present invention.

In FIG. 2, the same reference numerals are used to indicate the members or means corresponding to those in FIG. 1.

Disc 11 is rotatably mounted by bearings 11a. The motor 14 constituting a drive mechanism is connected to central shaft 11b of disc 11. A boss portion 11c of disc 11 is provided with terminals of film-like heater 10, which is embedded in the disc 11. The terminals are in contact with terminals of temperature control device 12, which includes a thermocouple for detecting the temperature of movable plate 1 and a controller for controlling the temperature of movable plate 1 heated by heater 10.

In FIG. 3, the same reference numerals are used to indicate the members or means corresponding to those in FIG. 1 or FIG. 2.

Cylindrical drum 21 is carried by horizontal rotary shafts 21a, 21b, which are mounted on bearings 21c. Shaft 21a is connected to an output shaft of motor 14, which constitutes a drive mechanism, so that drum 21 is rotated by motor 14. The interior of drum 21 is provided with film-like heater 10 along the inner surface of the cylindrical wall. An extension of shaft 21a is provided with terminals of heater 10, which are in contact with terminals of temperature control device 12. Control device 12 includes a thermocouple for detecting the temperature of the movable plate 1 and a controller for controlling the temperature of the drum 21 heated by heater 10.

The sliding part and the pushing part preferably have high chemical stability, thermal shock resistance, mechanical shock resistance, and abrasion resistance. They are preferably made of a metal, ceramic, polymer substance, or a composite thereof.

When a metal is used it can be used either without any treatment or as coated with another metal by vapor depositions or plating.

Polymer substances can include addition polymers of vinyl compounds such as polyethylene, polystyrene, poly(meth)acrylic acid, poly(meth)acrylic ester, polyvinyl acetate, polyacrylonitrile and polyhalogenated vinyl, interpolymers of fluorinated vinyl compound with ethylene, vinylidene cyanide and the like, chemical compounds including fluorine such as polytrifluoroethylene, polytetrafluoroethylene and polyhexafluoropropylene, polyesters, polycarbonates and polyethers such as polyamide, polyimide, polyurethane and polyethylene terephthalate, and heat-hardening resins such as unsaturated polyester, epoxy and bakelite. The polymer substaces can be used either without any treatment for the surfaces of the sliding part and the pushing part, or after being subjected to one of the processes described below in response to their intended use.

When films of polymer substances are attached to the opposed surfaces of the sliding part and the pushing part, these films can be used either without any treatment or after being subjected to alkaline metal solvent treatment, treatment by the alkaline metal amalgam process, chemical etching by, for example, the electrolylic process, vapor deposition of silver, aluminium or the like, vacuum discharge treatment, sputter etching (coating), corona discharge treatment, graft treatment, plasma spray coating, sandblast treatment, chemical treatments for making films porous, and the like.

The substance to be used is preferably selected by comparing the results of organoleptie test with the test results obtained by the apparatus according to the invention. Generally chemically etched or sputter-etched films including fluorine are most preferable.

EXAMPLE 1

Sputter-etched films were obtained by sputtering PTFE virgin films by use of a sputtering apparatus. The original thickness of the films was about 15 $\mu$m. SEM (scanning electron microscope) observation of the films showed it to have many fibres of 0.5 to 1.0 $\mu$m length uniformly distributed over the surfaces. The surfaces were hydropihlic. The films were attached to the opposed surfaces of the movable plate 1 and the pushing part 2 shown in FIG. 1.

A commercial cosmetic cream "M" was applied to the sliding surface of the movable plate 1 and tested by the apparatus according to the procedure described earlier. The sliding rate of the movable plate 1 was 9 reciprocations per minute and the number of reciprocations was 230.

During the test, the force applied to the movable plate 1 in the sliding direction was measured by the strain gauge 3. In addition, four samples of the emulsion were taken during the test and observed by an optical microscope. The results are shown in FIG. 4 and FIG. 4a through 4e.

Figure 4:
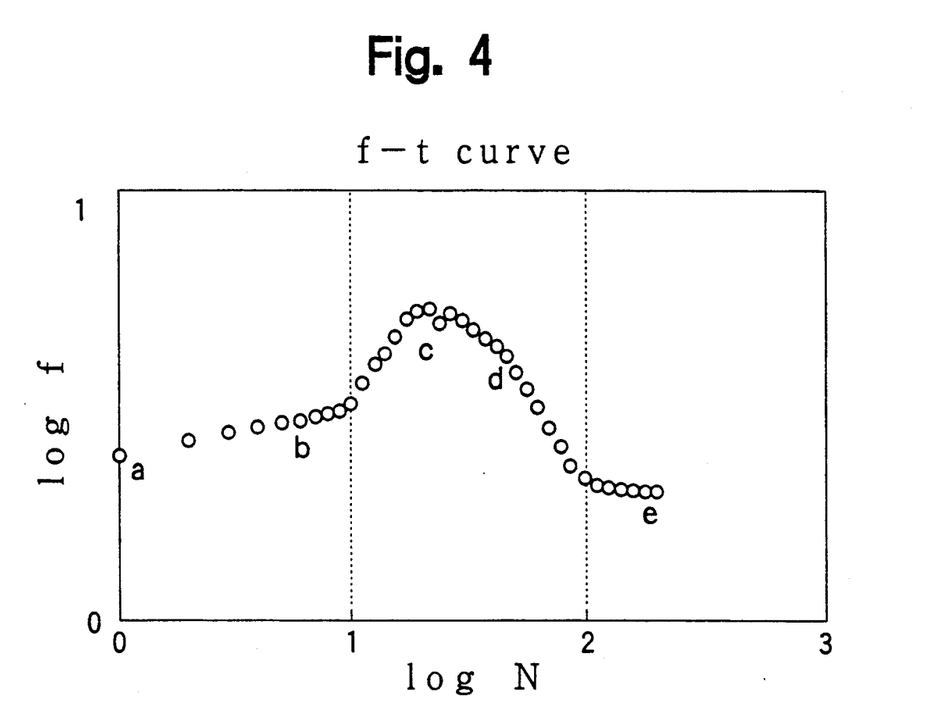
FIG. 4 and FIGS. 4a–4e illustrate the relationship between the measured shearing force and the microscopic state of a commercial cosmetic cream "M".
Figure 4A:
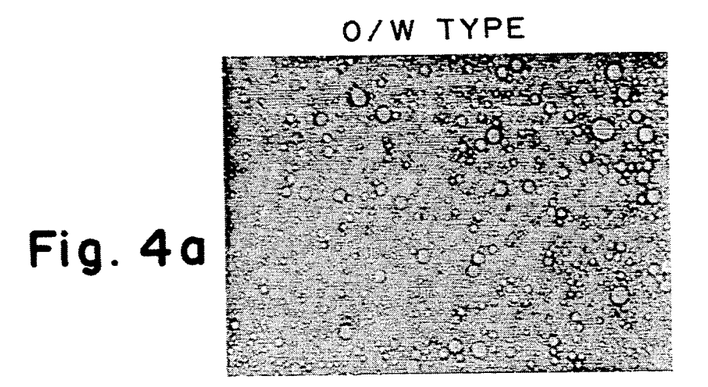
Figure 4B:
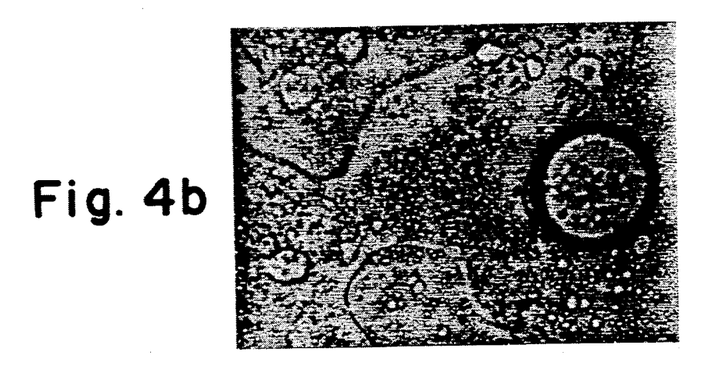
Figure 4C:
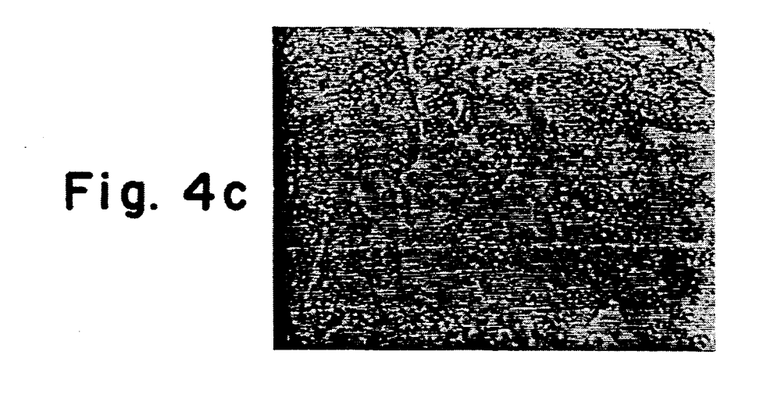
Figure 4D:
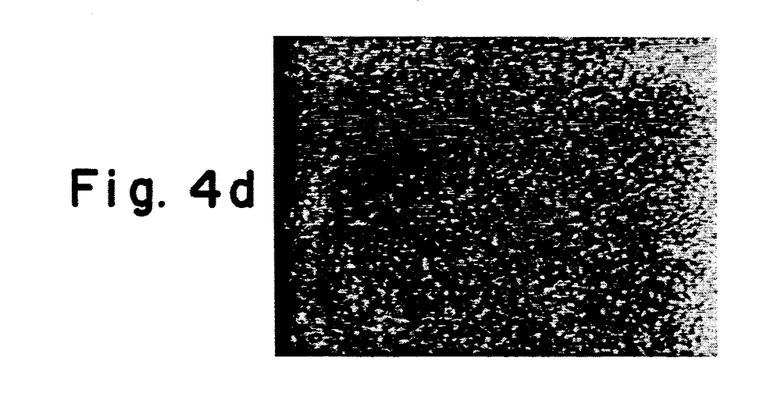
Figure 4E:
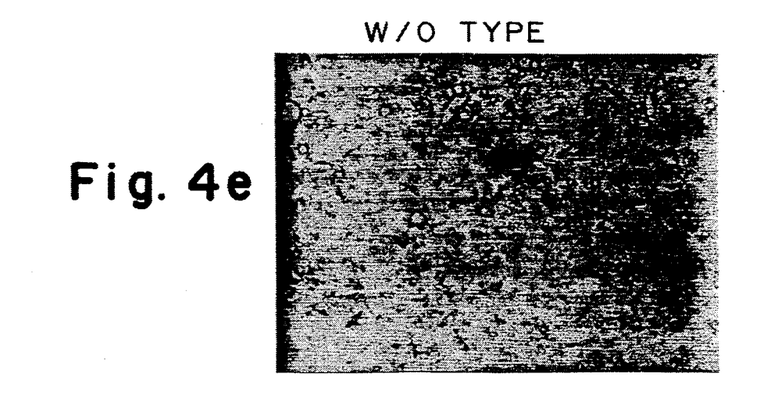

In FIG. 4, the horizontal axis represents the logarithm (log N) of the number of reciprocations of the movable plate 1 and the vertical axis represents the logarithm (log f) of the measured shearing force. Points "a", "b", "c", "d" and "e" in the same figure are the points at which samples were taken during the test. The five microphotographs "a" through "e" in FIG. 4a through 4e correspond to the sampling points.

As is apparent from these microphotographs, the cream was an oil-in-water type (hereinafter called O/W type) emulsion at point "a" (the starting point). At point "b" it was still of O/W type but had partially changed to water-in-oil-in-water type (W/O/W type). Between points "c" and "d", the phase was in the process of changing from O/W type to water-in-oil type (W/O type). At point "e", the phase had fully changed to W/O type. Accordingly, the cream was found to be an emulsion which could be changed from O/W type to W/O type.

A comparison of these microphotographs in FIG. 4a through 4e with FIG. 4 shows that the viscosity of the cream gradually increased with cohesion and coalescence of the oil droplets (from point "a" to "b") and that the viscosity then sharply increased with the dispersion of water droplets into the oil phase which had expanded in the manner of an oil film (points "b" to "c"). The latter process constitutes a phase change from O/W type to W/O type. After the phase change, the viscosity decreased as the water droplets rapidly became extremely fine (points "d" to "e"). Finally, the cream was fully changed to a W/O emulsion (point "e"). At this point, no further change occurred in the viscosity.

These results show that the apparatus according to this invention is capable of positively determining emulsion phase change and of continuously measuring the dynamic characteristics of the phase change.

EXAMPLE 2

Chemically etched films were obtained by treating PTFE virgin films with a complex solution of naphthalene and metallic sodium in tetrahydrofuran and then rinsing them with water. While no substantial change in the surfaces of the films could be observed by a SEM, the color of the films changed from white to brown and the surface became hydrophilic. The films were attached to the opposed surfaces of the movable plate 1 and the pushing part 2 of the same apparatus as in Example 1.

Two kinds of commercial nutrient creams "A" and "B" and two kinds of commercial cleansing creams "C" and "D" were tested under the same conditions as in Example 1. All of the creams were O/W type emulsions. The results obtained are shown in FIGS. 5 and 6, in which the two axes are graduated for the same parameters as in FIG. 4.

On the other hand, tactile testing of the creams was conducted by five female panelers. The results obtained are shown in Table 1.

Figure 5:
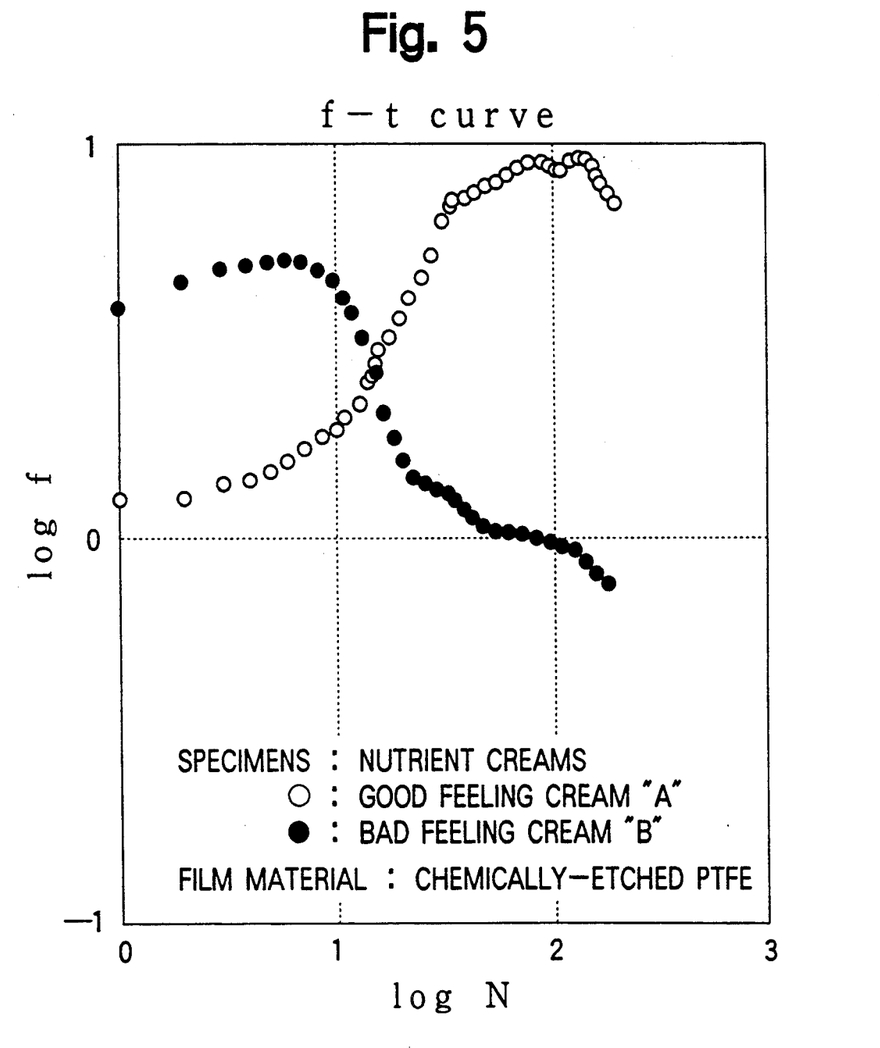
FIG. 5 illustrates the relationship between the number of reciprocations and the measured shearing force in the case of commercial nutrient creams "A" and "B".
Figure 6:
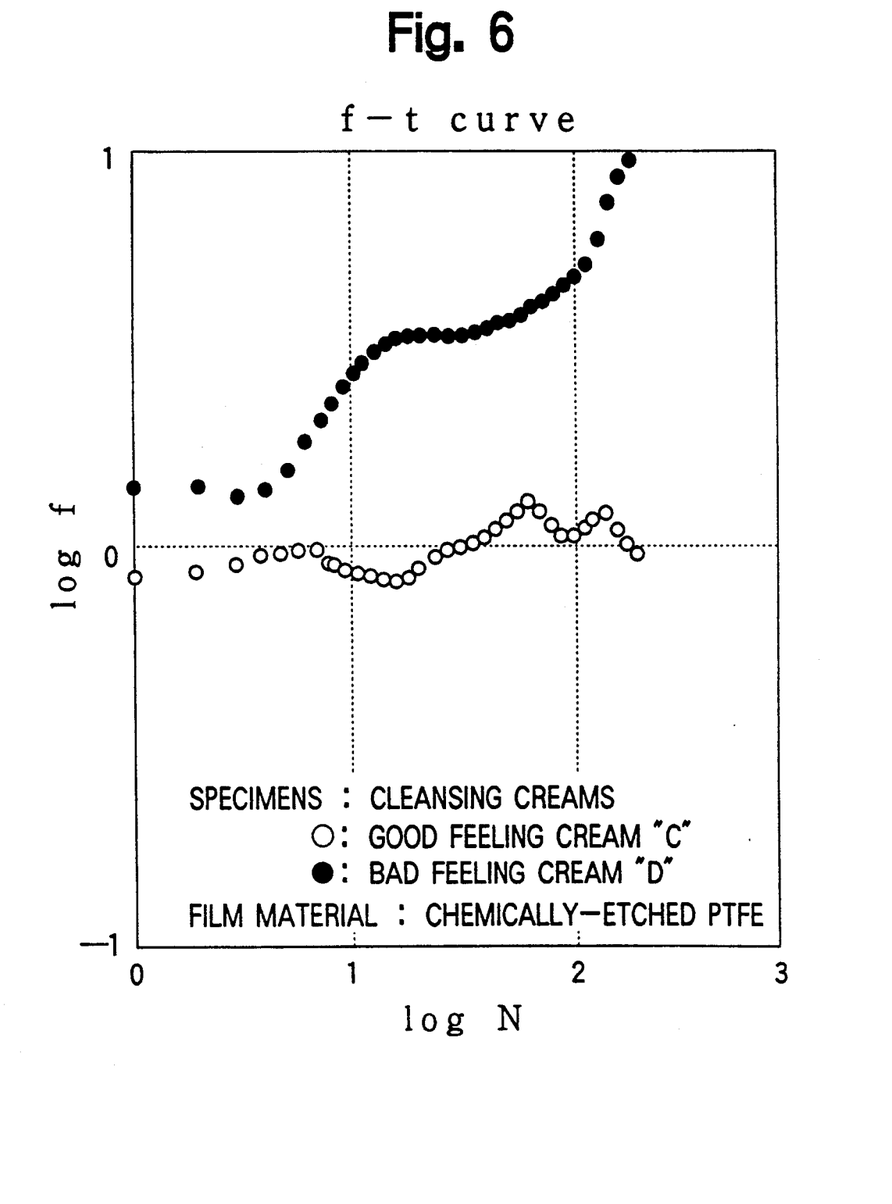
FIG. 6 illustrates the relationship between the number of reciprocations and the measured shearing force in the case of commercial cleansing creams "C" and "D".

As is apparent from FIGS. 5 and 6, there are significant differences in shear force between the creams "A" and "C" which the panelers rated us having a "good feeling" and the creams "B" and "D" which they rated as having a "bad feeling". It will be noted that the shear forces obtained by the tests are in close agreement with the panelers' feelings shown in Table 1. It can therefore be conducted that the results obtained by the apparatus agree well with the "feelings" rated by the panelers.

As shown above, the apparatus can accurately evaluate emulsion phase change and can therefore replace panelers in the evaluation of emulsions.

TABLE 1

| Results of organoleptic test of 4 creams by panel of experts | |
|---|---|
| Nutrient Cream A | organoleptic test + |
| Good feeling. Soft from the beginning and easy to spread on the skin. Someone can feel a refreshed skin. Not sticky after application. | |
| Nutrient Cream B | organoleptic test − |
| Bad feeling. Hard to spread at first but suddenly becomes soft and slippery during the use. Sticky after application. | |
| Cleansing Cream C | organoleptic test + |
| Good feeling. Soft and easy to spread on the skin from the start and throughout use. Stays soft after application. Easy to wipe off and wash away. | |
| Cleansing Cream D | organoleptic test − |
| Bad feeling. Although soft and easy to spread on the skin at the start, it becomes hard to massage the face during use. Difficult to wipe off and wash away. | |

EXAMPLE 3

Chemically etched films were obtained by treating PTFE virgin films with a liquid ammonium solution of metallic sodium in tetrahydrofuran as in Example 2. In addition, porous films were obtained by heat stretching PTFE film. The chemically etched films, the porous films and the sputter-etched films obtained in Example 1 were attached to the opposed surfaces of the movable plate 1 and the pushing part 2 of the same apparatus as in Example 1. A commercial nutrient cream "A" was tested by the apparatus with air being blowing onto the cream. The surfaces of the pretreated PTFE films, the sputter-etched films and the porous films were fluorines, and that of the chemically etched film was carbons. The observation of the films showed that the surfaces of the pretreated PTFE films and the chemically etched films were generally smooth and that of the sputter-etched films had many fibres of 1.0 to 1.5 μm length, and that of the porous films had many holes of about 2 μm diameter.

Figure 7:
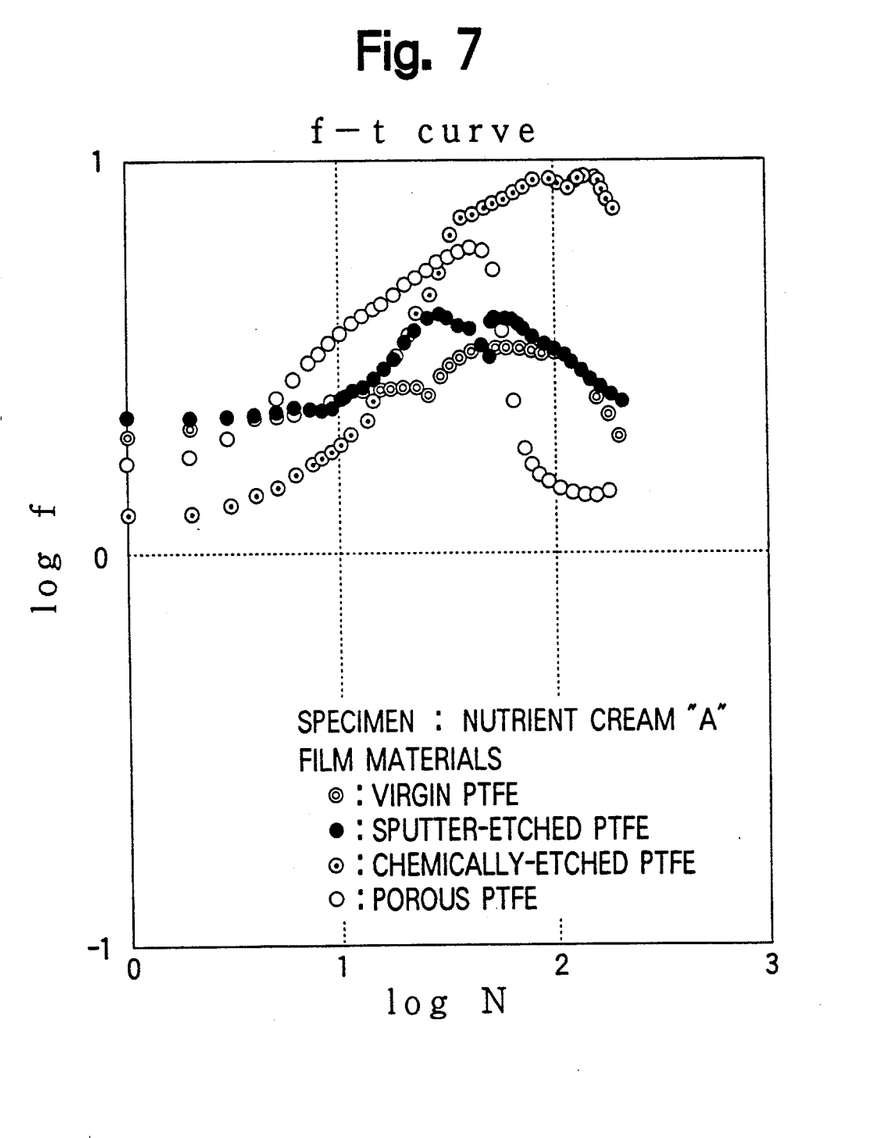
FIG. 7 illustrates the relationship between the number of reciprocations and the measured shearing force in the case of commercial nutrient cream "A", in which four different films are used.

The test results obtained are shown in FIG. 7. From the figure, it is found that the phase change behavior of the emulsion is influenced by the compositions and the structures of the surface materials. It also means that the phase change is influenced by the compositions and the cofigulations of the emulsion created at the initial stage of the phase change.

EXAMPLE 4

The sputter-etched films obtained in Example 1 were attached to the opposed surfaces of the disc 11 and the pushing part 2 of the apparatus shown in FIG. 2 and a commercial nutrient cream "G" was tested by the apparatus at room temperature with air being blown onto the cream. The disc 11 was rotated at 9 revolutions per minute (rpm) and the number of rotations was 230.

Figure 8:
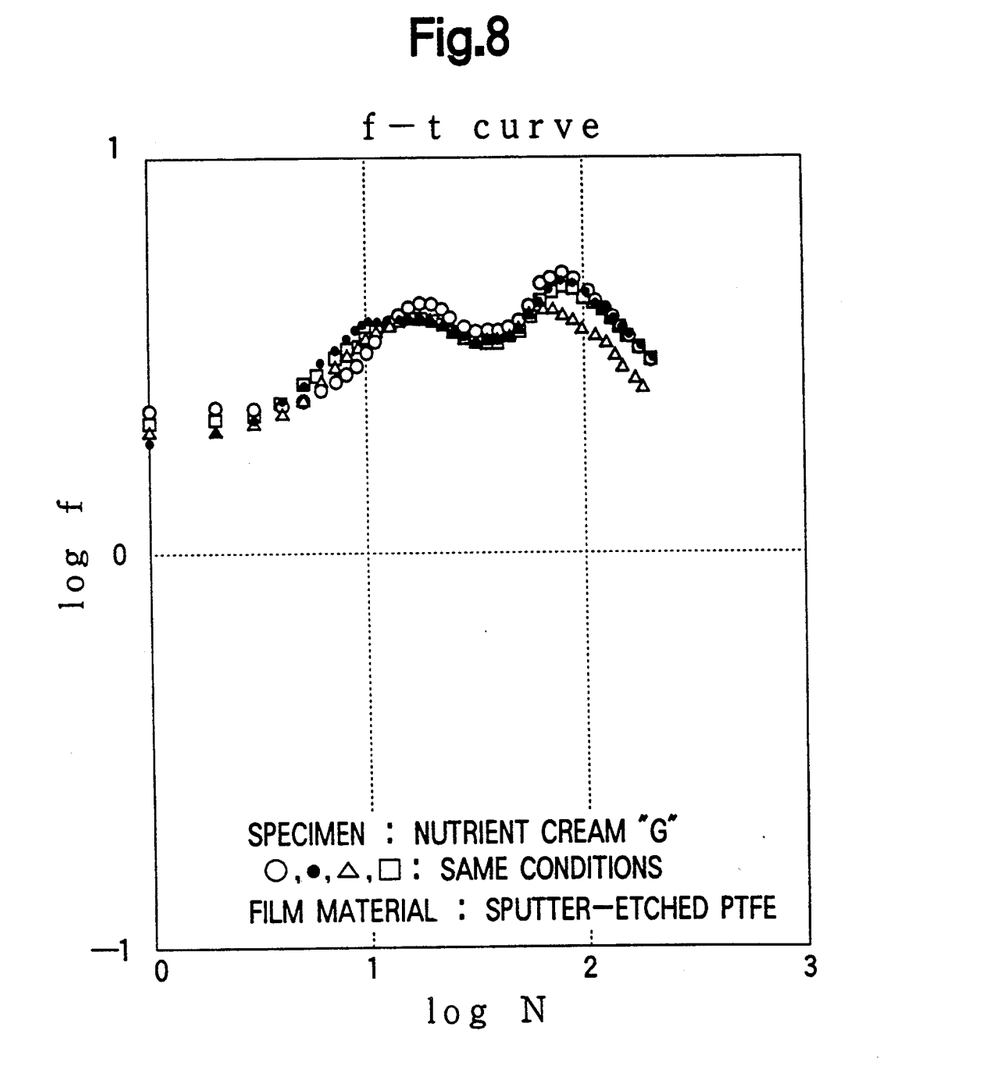
FIG. 8 illustrates the relationship between the number of rotations and the measured shearing force in the case of a commercial nutrient cream "G".

The results obtained are shown in FIG. 8. In the figure, the horizontal axis is graduated for the logarithm (log N) of the number of rotations of the disc 11 and the vertical axis for the logarithm (log f) of the measured shearing force.

From FIG. 8, it is apparent that the phase change behavior of an emulsion can also be determined by the apparatus of FIG. 2.

EXAMPLE 5

Figure 9:
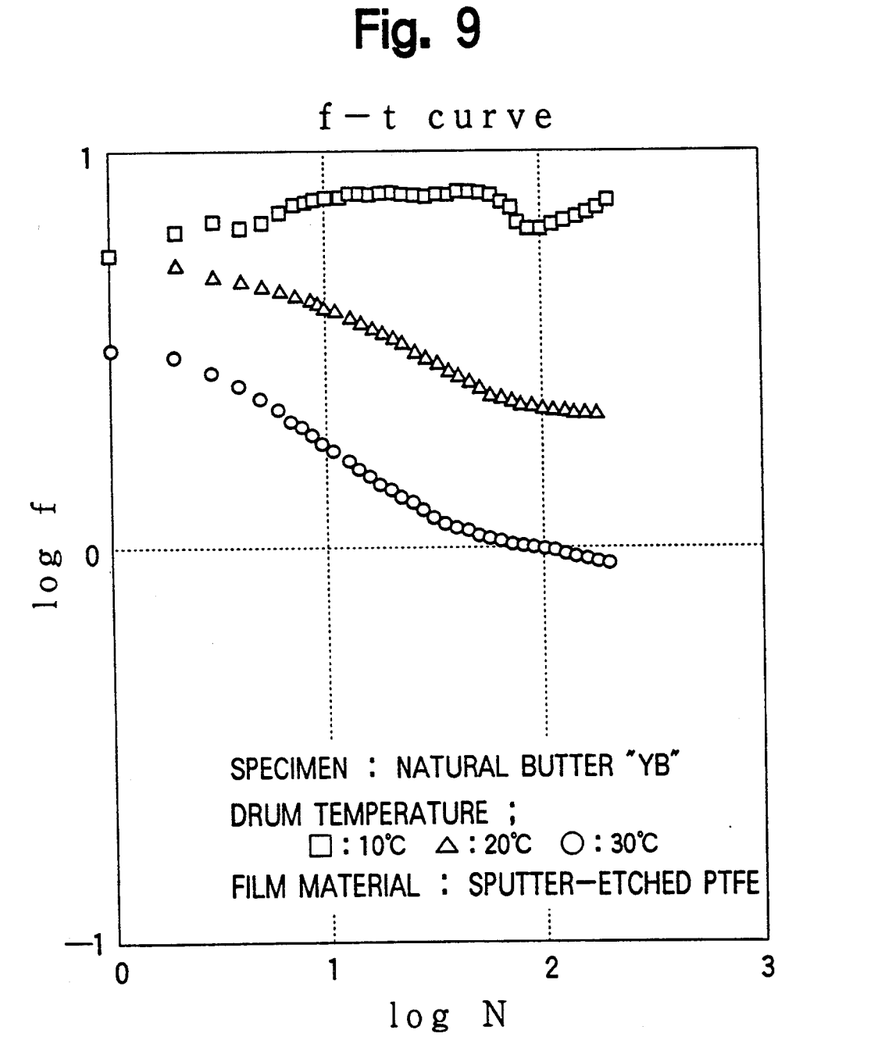
FIG. 9 illustrates the relationship between the number of rotations and the measured shearing force in the case of a commercial natural butter "YB".

The sputter-etched films obtained in Example 1 were attached to the opposed surfaces of the drum 21 and the pushing part 2 of the apparatus shown in FIG. 3 and a commercial natural butter "YB" was tested by the apparatus. The drum was rotated at 9 rpm and the number of rotations was 230. The test results are shown in FIG. 9, in which the two axes represent the same parameters as in FIG. 8.

The butter is a W/O type emulsion of water droplets dispersed in animal oil. The butter do not change phase in the temperature range of the test. Therefore the figure merely shows the changes in viscosity. As seen from FIG. 9, there was no change in viscosity under 10° C. while at over 20° C. the viscosity decreased with increasing number of rotations.

On the other hand, organoleptic test conducted by a panel on the butter under 20° C. and over 25° C. showed it to be too soft to keep its shape over 25° C. Comparing this result with the results in FIG. 9 shows that the test results by the apparatus correspond to human feelings.

Although treated polymer films were attached to the opposed surfaces of the sliding part and the pushing part in the Example 1-5, the opposed surfaces contacting with the emulsion can be treated in response to their intended use and used for evaluating phase change of the emulsion.

The invention has thus been shown and described with reference to specific structures. However, it should be noted that the invention is in no way limited to the details of the illustrated structures but changes and modification may be made without departing from the scope of the appended claims.

We claim:

1. An apparatus for evaluating a phase change of an emulsion, said apparatus comprising:
   a sliding part having a sliding surface to which said emulsion is applied;
   a pushing part movable toward the sliding surface and having a surface opposed to the sliding surface, said pushing part for pushing against the emulsion on the sliding surface at a predetermined position so that said emulsion is disposed between said sliding surface and said surface of said pushing part and contacts said surfaces during the sliding movement of the sliding surface whereby phase of the emulsion is changed to a different phase of the emulsion; and
   sensor means for measuring a force acting on the pushing part in the sliding direction during phase change of the emulsion, said sensor being used for evaluating the phase change of the emulsion from change in the measured force;
   wherein the sensor means continuously measures the force to detect dynamic characteristics of the force, said dynamic characteristics being compared with one of standard data and data regarding a preliminarily measured force for the emulsion.

2. An apparatus in accordance with claim 1, wherein a film of a polymer substance is connected to at least one of said sliding surface and said surface of said pushing part.

3. An apparatus in accordance with claim 2, wherein said at least one film is a chemically etched polymer film.

4. An apparatus in accordance with claim 2, wherein said at least one film is a sputter-etched polymer film.

5. An apparatus in accordance with claim 1, further comprising fan means for blowing air onto the emulsion to evaporate its volatile components.

6. An apparatus in accordance with claim 1, wherein the sliding part is a reciprocating movable plate.

7. An apparatus in accordance with claim 1, wherein the sliding part is a rotatable disc.

8. An apparatus in accordance with claim 1, wherein the sliding part is a rotatable cylindrical drum.

9. A method for evaluating a phase change of an emulsion, said method comprising the steps of:
   applying emulsion to a sliding surface of a sliding part;
   sliding said sliding part in a direction parallel to said sliding surface;
   pushing part so that a surface of said pushing part opposed to said sliding surface is brought into contact with the emulsion on the sliding surface at a predetermined position during sliding movement of the sliding surface, whereby changing the phase of the emulsion disposed between the sliding surface and the surface of the pushing part to a different phase thereof;
   measuring a force acting upon the pushing part in the sliding direction, and
   evaluating the phase change of the emulsion from change in the measured force, said evaluating step including the step of comparing dynamic characteristics of the force with one of standard data and data regarding a preliminarily measured force on the emulsion.

10. An apparatus in accordance with claim 1, further comprising means for elastically biasing the pushing part toward the sliding surface.

11. An apparatus in accordance with claim 10, wherein said elastically biasing means is a spring.

12. An apparatus in accordance with claim 1, wherein said pushing part includes a shaft and said apparatus includes means for supporting said shaft so that said pushing part can move toward and apart from the sliding surface but cannot move in the sliding direction.

13. An apparatus in accordance with claim 12, wherein said supporting means is a bearing.

14. An apparatus in accordance with claim 12, further comprising means for moving said shaft in a direction perpendicular to said sliding direction; and
   means for elastically biasing said pushing part.

15. A method in accordance with claim 9, wherein said pushing step includes elastically biasing said pushing part.

16. A method in accordance with claim 9, wherein said pushing step includes supporting a shaft of said pushing part so that the pushing part can move perpendicularly to said direction but not in said direction.

17. A method in accordance with claim 16, wherein said pushing step includes moving said shaft perpendicular to said direction using means for elastically biasing said pushing part.

18. An apparatus in accordance with claim 1, further comprising temperature controlling means for controlling the temperature of the sliding part between −20° C. and 100° C.

* * * * *

UNITED STATES PATENT AND TRADEMARK OFFICE
CERTIFICATE OF CORRECTION

PATENT NO. : 5,319,958

DATED : June 14, 1994

INVENTOR(S) : Munehiro DATE and Yukio INABA

It is certified that error appears in the above-identified patent and that said Letters Patent is hereby corrected as shown below:

On the Title page at item [75] Inventors:

correct the second inventor's name to read — Yukio INABA —

Signed and Sealed this

Eighth Day of November, 1994

*Attest:*

BRUCE LEHMAN

*Attesting Officer*    *Commissioner of Patents and Trademarks*